United States Patent
Sharp et al.

(10) Patent No.: US 9,381,007 B2
(45) Date of Patent: Jul. 5, 2016

(54) TISSUE RETRACTOR AND METHOD OF USE THEREOF

(75) Inventors: Bradley J. Sharp, Irvine, CA (US); Wayne A. Noda, Mission Viejo, CA (US); Stephen G. Bell, Eur Roma (IT)

(73) Assignee: Specialty Surgical Instrumentation Inc., Antioch, TN (US)

( * ) Notice: Subject to any disclaimer, the term of this patent is extended or adjusted under 35 U.S.C. 154(b) by 1262 days.

(21) Appl. No.: 12/812,310

(22) PCT Filed: Jan. 9, 2009

(86) PCT No.: PCT/SG2009/000019
§ 371 (c)(1),
(2), (4) Date: Jul. 9, 2010

(87) PCT Pub. No.: WO2009/088376
PCT Pub. Date: Jul. 16, 2009

(65) Prior Publication Data
US 2010/0286481 A1    Nov. 11, 2010

(51) Int. Cl.
*A61B 1/32* (2006.01)
*A61B 17/02* (2006.01)
(Continued)

(52) U.S. Cl.
CPC .............. *A61B 17/02* (2013.01); *A61B 17/085* (2013.01); *A61B 2017/00407* (2013.01); *A61B 2017/0287* (2013.01)

(58) Field of Classification Search
USPC ......... 606/184, 201–249, 279, 119, 121, 193, 606/204.35; 602/41, 53–54; 600/201–249
See application file for complete search history.

(56) References Cited

U.S. PATENT DOCUMENTS 2,493,598 A * 1/1950 Rozek ........................... 600/229
3,736,925 A * 6/1973 Erman ..................... 606/204.35
(Continued)

FOREIGN PATENT DOCUMENTS

DE   32 34 875    3/1984
EP   1011467      8/2008
(Continued)

OTHER PUBLICATIONS

International Preliminary Report on Patentability issued in PCT/US2009/000019 dated Apr. 16, 2010 (Form PCT/IPEA/409).
(Continued)

*Primary Examiner* — Todd E Manahan
*Assistant Examiner* — Jessica Weiss
(74) *Attorney, Agent, or Firm* — Hayes Soloway, P.C.

(57) ABSTRACT

A tissue retractor is disclosed. The tissue retractor includes: a base support unit having an underside that is adapted to be conformable and to be removably attachable to a surface proximate to an incision; and a retractable member substantially inelastic in its central longitudinal axis and flexible in at least one axis deviating from said central longitudinal axis, wherein the retractable member is adapted to receive the mounting portion of an at least one tissue hook, the at least one tissue hook having a tissue engagement portion and a mounting portion, wherein the tissue engagement portion is capable of engaging tissue to be retracted, wherein said retractable member is retractable away from the incision, such that the tissue engagement portion of the tissue hook retracts tissue to which it is engaged, wherein said retractable member has a first end and a second end, wherein said retractable member is integrally formed with the base support unit via the first end, and wherein the second end of the retractable member has a securing mechanism for removably attaching the second end to a corresponding securing mechanism on the first end and/or the base support unit.

4 Claims, 5 Drawing Sheets

STANDARD REETRAKT

(51) Int. Cl.
 *A61B 17/08* (2006.01)
 *A61B 17/00* (2006.01)

(56) References Cited

U.S. PATENT DOCUMENTS

| | | | |
|---|---|---|---|
| 3,970,075 A | | 7/1976 | Sindelar et al. |
| 5,476,478 A | * | 12/1995 | Jackson .................. 606/204.35 |
| 5,676,137 A | * | 10/1997 | Byrd ....................... 128/207.17 |
| 5,728,047 A | | 3/1998 | Edoga |
| 5,964,698 A | * | 10/1999 | Fowler ......................... 600/217 |
| 6,416,504 B2 | * | 7/2002 | Mosel et al. ................. 604/528 |
| 8,262,567 B2 | | 9/2012 | Sharp et al. |
| 2004/0186356 A1 | * | 9/2004 | O'Malley et al. ............. 600/231 |
| 2005/0197537 A1 | | 9/2005 | Bonadio et al. |
| 2008/0103366 A1 | * | 5/2008 | Banchieri et al. ............ 600/208 |
| 2009/0198107 A1 | * | 8/2009 | Park et al. ..................... 600/215 |

FOREIGN PATENT DOCUMENTS

| | | | | |
|---|---|---|---|---|
| GB | 2223410 | * | 4/1990 | ............ A61B 17/00 |
| WO | 03013368 | | 2/2003 | |
| WO | 2007114982 | | 11/2007 | |

OTHER PUBLICATIONS

International Search Report in PCT/US2009/000019 dated Mar. 23, 2009 Form PCT/ISA/210).
Written Opinion of the International Preliminary Examining Authority in PCT/US2009/000019 dated Nov. 29, 2009.
Written Opinion of the International Searching Authority in PCT/US2009/000019 dated Mar. 23, 2009 (Form PCT/ISA/237).
Brad Sharp, Stephen Graham Bell, Wayne Artur Noda, Lazmikant Khanolkar, Meng Pheng Tan, Yin Chiang Boey, San Ma, Erwin Merijn Wouterson, "Tissue Retractor, Tissue Retractor Kit and Method of Use Thereof" file history of related U.S. Appl. No. 11/677,975, filed Feb. 22, 2007.

* cited by examiner

STANDARD REETRAKT

DRAPE REETRAKT

DRAPE REETRAKT ALTERNATE

DRAPE REETRAKT NON LOOPING

SKIN SURFACE RETRACTOR

TISSUE RETRACTOR AND METHOD OF USE THEREOF

CROSS-REFERENCE TO RELATED APPLICATIONS

This application is a national phase entry based on the International Patent Application PCT/SG2009/000019 that claims the priority of the U.S. provisional patent application 61/020,034 that was filed on Jan. 9, 2008. The entire content of this prior United States patent application is herewith incorporated by reference.

TECHNICAL FIELD

The present invention relates to the field of tissue retractors.

BACKGROUND OF THE INVENTION

Background

During the course of a surgical procedure, a surgeon opens tissue of a patient by first making at least one incision typically using a scalpel. After the incision is made in the tissue, retractors are then used to retract the periphery of the incision in order to open the incision further. Once retracted, the open incision allows the surgeon to access other tissues or organs within the body, for example. Apart from just providing access, the tissue retractors serve to stabilize and present said retracted tissue in an orientation that is optimal for the surgeon to operate on.

During the retraction of incised tissue, care must be taken to avoid inflicting new, or as the case may be, additional trauma such as bruising, for example. Bruising may also be caused by viscoelastic forces inherently present in the contracting muscles or tissues of the patient, as said contracting muscles or, tissues work against the forces exerted thereon by the refractor. Accordingly, it is important to exercise care in the application of external forces typically requiring additional operating personnel during surgical procedures in order to minimize the possibility of causing any bruising or even tearing of the tissue during surgery.

In addition to retracting incised tissue, retractors are also used for the general purpose of retracting tissue, i.e. tissue that is not necessarily incised.

In light of the above, it is thus advantageous to have a tissue refractor that is compact, has a low-profile, portable, cost-effective to manufacture and provides good tissue refraction leverage, as recognized by the present invention.

SUMMARY OF THE INVENTION

A first aspect of the invention relates to a tissue retractor including: a base support unit having an underside that is adapted to be conformable and to be removably attachable to a surface proximate to an incision; and a retractable member substantially inelastic in its central longitudinal axis and flexible in at least one axis deviating from said central longitudinal axis, wherein the retractable member is adapted to receive the mounting portion of an at least one tissue hook, the at least one tissue hook having a tissue engagement portion and a mounting portion, wherein the tissue engagement portion is capable of engaging tissue to be retracted, wherein said retractable member is retractable away from the incision, such that the tissue engagement portion of the tissue hook retracts tissue to which it is engaged, wherein said retractable member has a first end and a second end, wherein said retractable member is integrally formed with the base support unit via the first end, and wherein the second end of the retractable member has a securing mechanism for removably attaching the second end to a corresponding securing mechanism on the first end and/or the base support unit.

A second aspect of the invention relates to a method of retracting tissue with a tissue retractor. The tissue retractor comprises a base support unit having an underside that is adapted to be conformable and to be removably attachable to a surface proximate to an incision; and a retractable member substantially inelastic in its central longitudinal axis and flexible in at least one axis deviating from said central longitudinal axis, wherein the retractable member is adapted to receive the mounting portion of an at least one tissue hook, the at least one tissue hook having a tissue engagement portion and a mounting portion, wherein the tissue engagement portion is capable of engaging tissue to be retracted, wherein said retractable member is retractable away from the incision, such that the tissue engagement portion of the tissue hook retracts tissue to which it is engaged, wherein said retractable member has a first end and a second end, wherein said retractable member is integrally formed with the base support unit via the first end, and wherein the second end of the retractable member has a securing mechanism for removably attaching the second end to a corresponding securing mechanism on the first end and/or the base support unit. The method includes: attaching the base support unit on a mounting surface; connecting the retractable member to the mounting portion of the at least one tissue hook;

engaging the tissue hook with the tissue to be retracted; retracting the retractable member so that the tissue engagement portion of the tissue hook retracts the tissue to be retracted to a predetermined distance.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which.

DETAILED DESCRIPTION OF THE INVENTION

Figure 1:
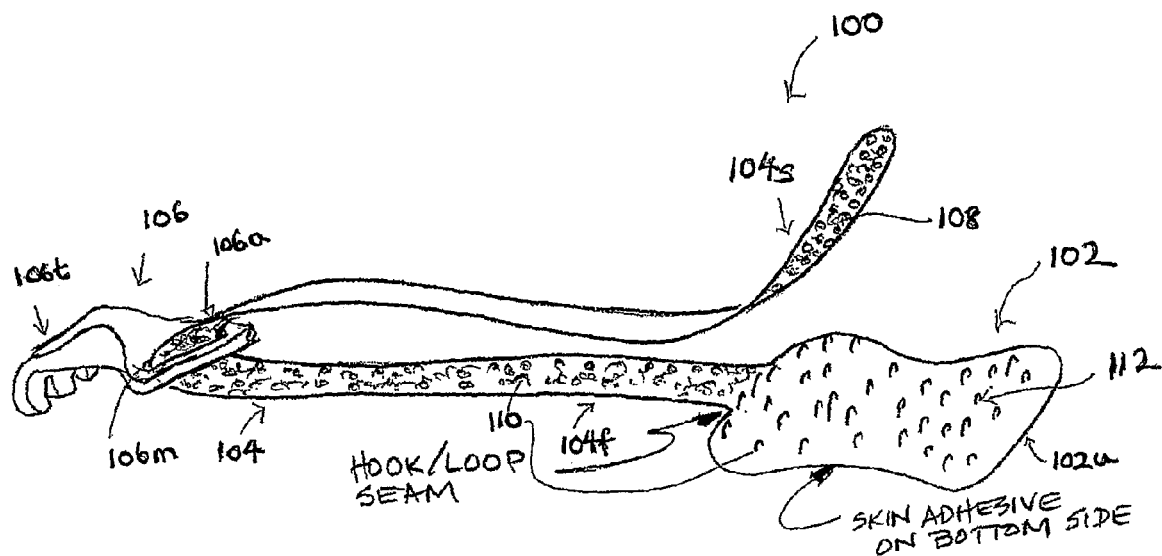
FIG. 1 shows a tissue retractor built in accordance with one embodiment of the present invention.

FIG. 1 shows a tissue retractor 100 built in accordance with one embodiment of the present invention.

The tissue retractor 100 includes a base support unit 102 having an underside 102u that is adapted to be conformable and to be removably attachable to a surface proximate to an incision (not shown). The tissue retractor 100 also includes a retractable member 104 substantially inelastic in its central longitudinal axis and flexible in at least one axis deviating from said central longitudinal axis. The retractable member 104 is adapted to receive the mounting portion 106m of an at least one tissue hook 106, the at least one tissue hook 106 having a tissue engagement portion 106t and a mounting portion 106m, wherein the tissue engagement portion 106t is capable of engaging tissue (not shown) to be retracted. The retractable member 104 is retractable away from the incision (not shown), such that the tissue engagement portion 106t of the tissue hook 106 retracts tissue (not shown) to which it is engaged. The retractable member 104 has a first end 104f and a second end 104s. The retractable member 104 is integrally formed with the base support unit 102 via the first end 104f, and the second end 104s of the retractable member 104 has a securing mechanism 108 for removably attaching the second end 104s to a corresponding securing mechanism 110 on the first end 104f and/or the base support unit 102.

The base support unit 102 has a corresponding securing mechanism 112 to the securing mechanism 108 on the second end 104s of the retractable member 104.

In another embodiment of the invention, the second end 104s of the retractable member 104 has a corresponding securing mechanism.

Examples of the securing mechanism 108 and the corresponding securing mechanism 112 include at least one of an adhesive surface, complimentary interlocking surfaces, a pawl mechanism, and a ratchet and teeth arrangement.

Examples of the complimentary interlocking surfaces include any of a hook and loop fastener and a duo lock mechanism. An example of the hook and loop fastener includes Velcro.

At least one tissue hook 106 may be connected to the retractable member 104.

The at least one tissue hook 106 has a tissue engagement portion 106t and a mounting portion 106m, wherein the tissue engagement portion 106t is capable of engaging at least a portion of tissue to be retracted (not shown).

The second end of the retractable member 104s may be looped back for securing with either the base support unit 102 or the first end 104f via an aperture 106a on the mounting portion 106m of the tissue hook 106.

The second end 104s of the retractable member 104 having a securing mechanism 108 for removably attaching the second end 104s to the corresponding securing mechanism 110 on the first end 104f and/or the base support unit 102 provides the advantage of leverage for retraction of tissue (not shown) held by the tissue retractor 100. This is because the leverage of having the retractable member 104 loop and fasten on itself provides a mechanical advantage in line with a pulley system, where the attachment strength required to secure the second end 104s of the retractable member 104 to the first end 104f and/or the base support unit 102 is half the tension force on the tissue retractor 100 tip. Further, such a retractable member 104 arrangement provides, from a singular strip, variable adjustment of the length from which the tissue retractor 104 is spaced from the base support unit 102. A compact design is thus achieved.

Figure 2:
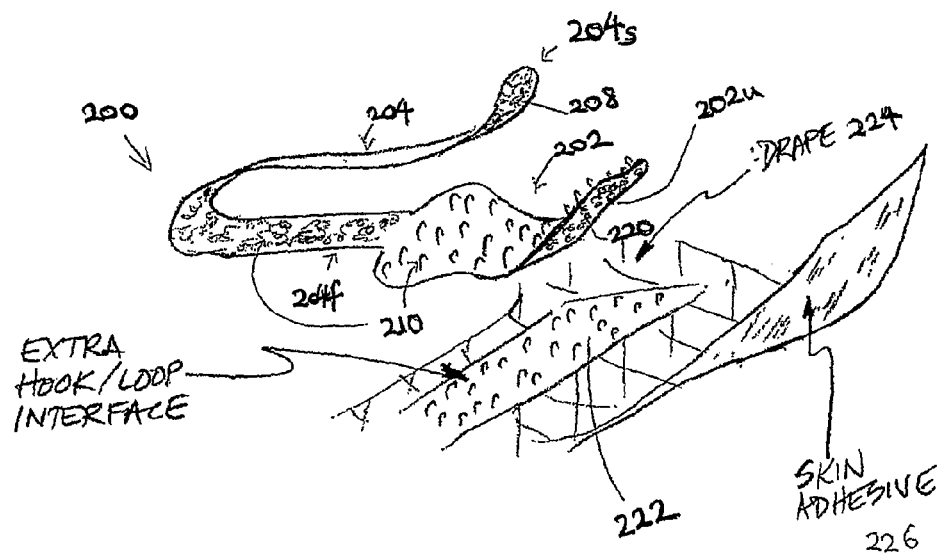
FIG. 2 shows a tissue retractor built in accordance with one embodiment of the present invention.

FIG. 2 shows a tissue retractor 200 built in accordance with one embodiment of the present invention.

The tissue retractor 200 includes a base support unit 202 having an underside 202u that is adapted to be conformable and to be removably attachable to a surface proximate to an incision (not shown). The tissue retractor 200 also includes a retractable member 204 substantially inelastic in its central longitudinal axis and flexible in at least one axis deviating from said central longitudinal axis. The retractable member 204 is adapted to receive the mounting portion of an at least one tissue hook (not shown).

The retractable member 204 has a first end 204f and a second end 204s. The retractable member 204 is integrally formed with the base support unit 202 via the first end 204f, and the second end 204s of the retractable member 204 has a securing mechanism 208 for removably attaching the second end 204s to a corresponding securing mechanism 210 on the first end 204f and/or the base support unit 202.

The underside 202u of the base support unit 202 has a second securing mechanism 220 for removably attaching the retractable member 204 to a surgical drape 224 via a third securing mechanism 222, the third securing mechanism 222 being of a structure that is complimentary to the second securing mechanism 220. The underside of the drape 224 has adhesive 226 that is suitable for adhering to skin. The surgical drape 224 is made of surgical grade plastic and/or paper material that is adapted to be conformable to a surface proximate to an incision (not shown).

Figure 3:
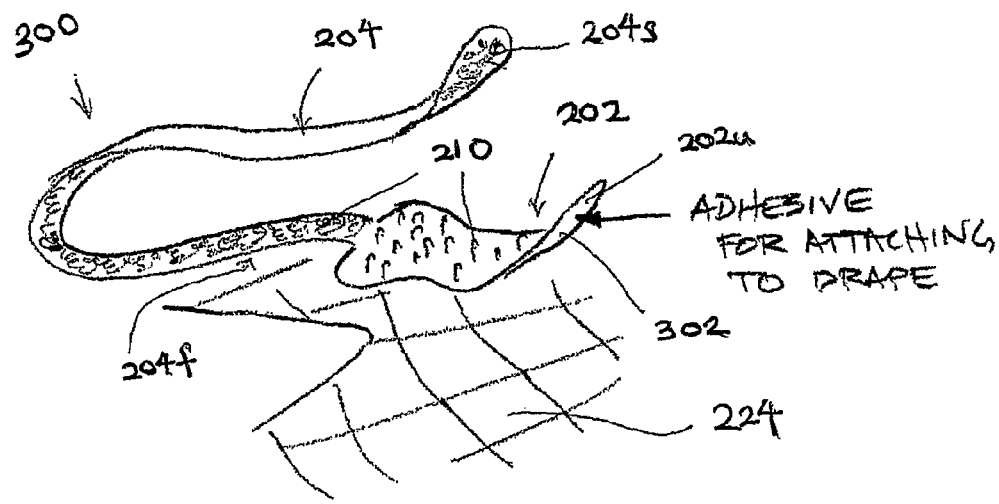
FIG. 3 shows a tissue retractor built in accordance with one embodiment of the present invention.

FIG. 3 shows a tissue retractor 300 built in accordance with one embodiment of the present invention.

The tissue retractor 300 is similar to the tissue retractor 200 shown in FIG. 2, therefore components having like reference numerals are not further elaborated.

The tissue retractor 300 differs from the tissue retractor 200 of FIG. 2 in that the tissue retractor 300 is attached to the drape 224 via an adhesive 302 that is on the underside 202u of the base support unit 202.

Figure 4:
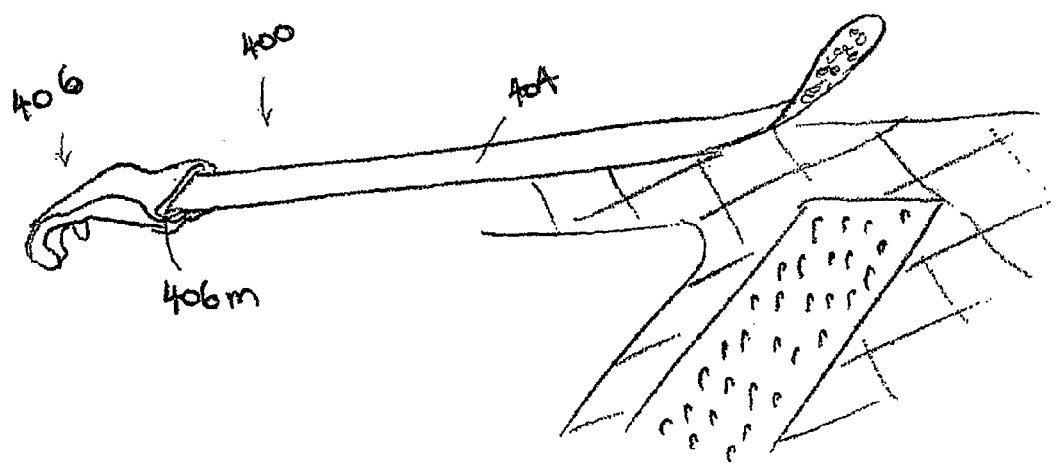
FIG. 4 shows a tissue retractor built in accordance with one embodiment of the present invention.

FIG. 4 shows a tissue retractor 400 built in accordance with one embodiment of the present invention.

The tissue retractor 400 includes a retractable member 404 substantially inelastic in its central longitudinal axis and flexible in at least one axis deviating from said central longitudinal axis. The retractable member 404 is adapted to receive the mounting portion 406m of an at least one tissue hook 406. The at least one tissue hook 406 is similar to the at least one tissue hook 106 of FIG. 1 and will therefore not be further elaborated.

Figure 5:
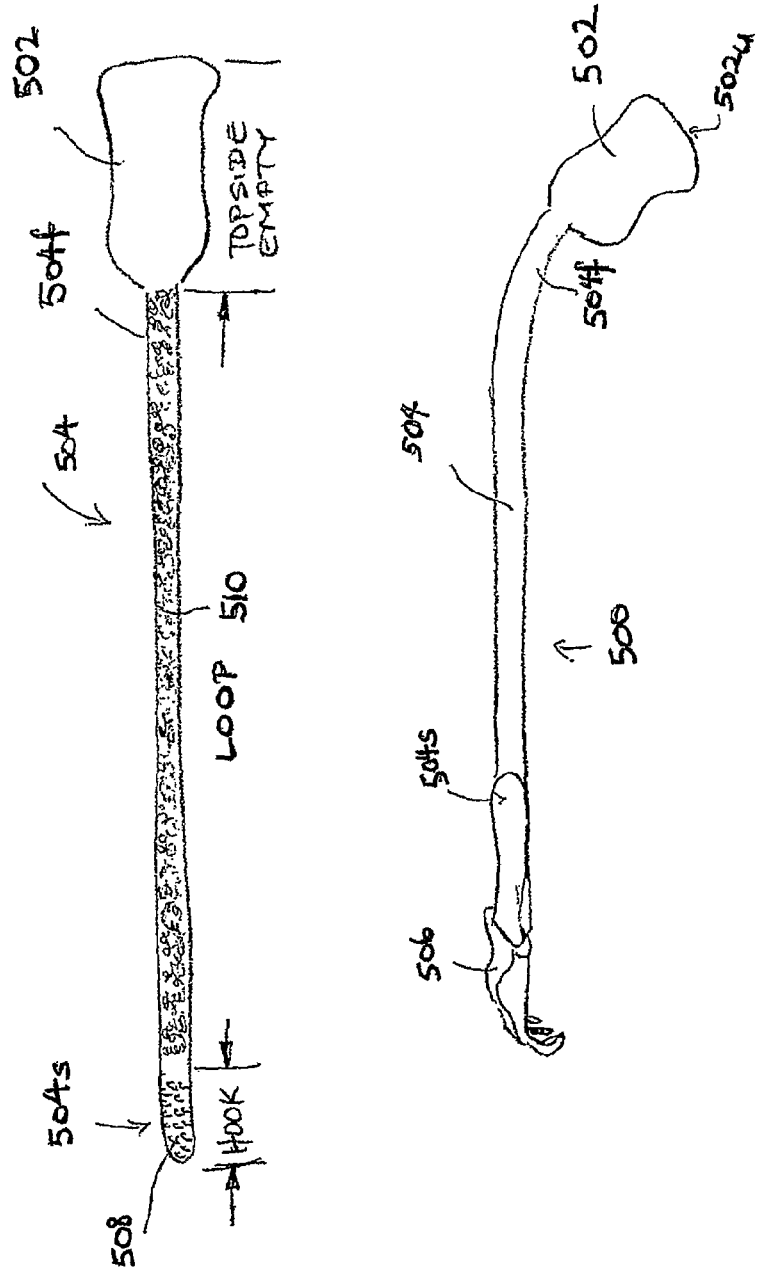
FIG. 5 shows a retractable member built in accordance with one embodiment of the present invention and a tissue retractor built in accordance with one embodiment of the present invention.

FIG. 5 shows a retractable member 504 built in accordance with one embodiment of the present invention and a tissue retractor 500 built in accordance with one embodiment of the present invention.

The tissue retractor 500 includes a base support unit 502 having an underside 502u that is adapted to be conformable and to be removably attachable to a surface proximate to an incision (not shown). The tissue retractor 500 also includes the retractable member 504 substantially inelastic in its central longitudinal axis and flexible in at least one axis deviating from said central longitudinal axis. The retractable member 504 is adapted to receive at least one tissue hook 506.

The retractable member 504 has a first end 504f and a second end 504s. The retractable member 504 is integrally formed with a base support unit 502 via the first end 504f, and the second end 504s of the retractable member 504 has a securing mechanism 508 for removably attaching the second end 504s to a corresponding securing mechanism 510 on the first end 504f. The corresponding securing mechanism 510 spans a substantial distance along the first end 504f towards the second end 504s.

The retractable member 504 allows for the tissue retractor 500 to be used in scenarios where the surface (not shown) the base support unit 502 is attached to is not proximate to an incision (not shown).

In addition to retracting incised tissue, the tissue retractors 100, 200, 300, 400 and 500 may be used for generic tissue retraction applications.

Figure 6:
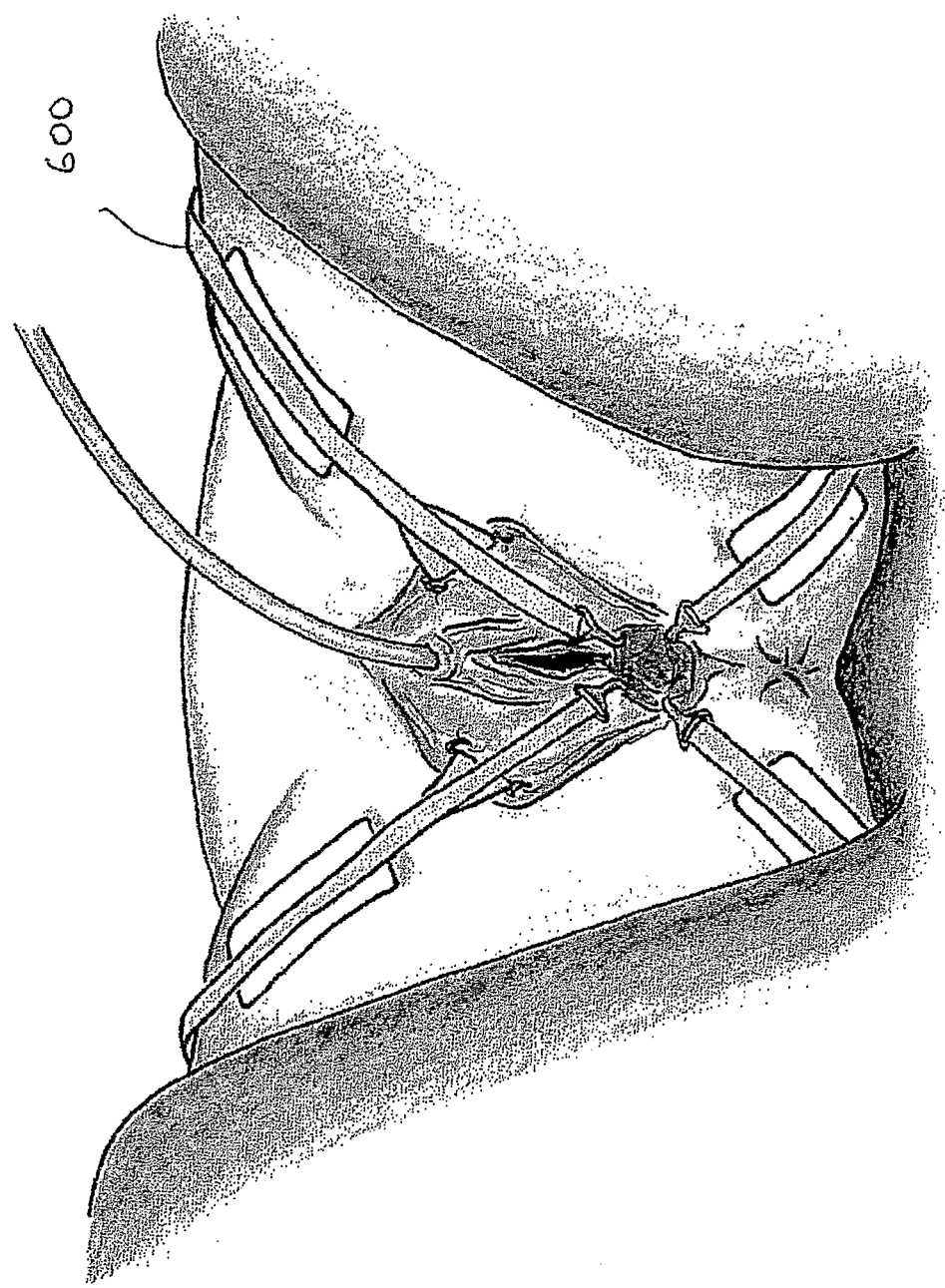
FIG. 6 shows a plurality of the tissue retractors, each built in accordance with embodiments of the present invention, used in vaginal prolapse.

FIG. 6 shows a plurality of the tissue retractors 600, each built in accordance with one embodiment of the present invention, used in vaginal prolapse. The tissue retractors 600 are used to retract the labia, rather than incised tissue. It is noted, in this context, that all kinds of tissue can be retracted with a tissue retractor as described herein.

The tissue retractors, may, for example, also be used in facial surgery (not shown), where the tissue hooks are used to retract tissue adjacent to the incision, rather than the incised tissue itself.

Figure 7:
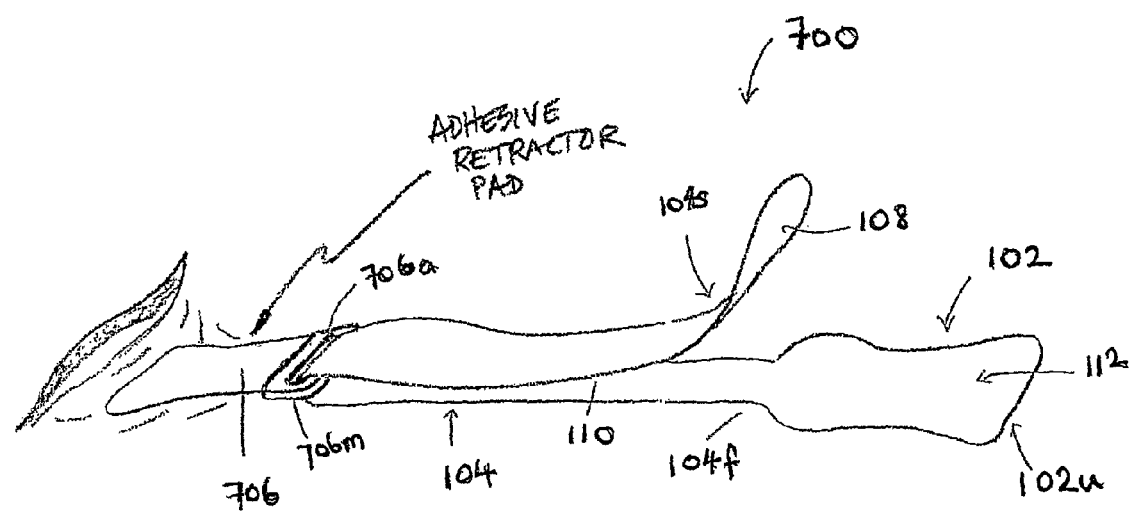
FIG. 7 shows a tissue retractor built in accordance with one embodiment of the present invention.

FIG. 7 shows a tissue retractor 700 built in accordance with one embodiment of the present invention.

The tissue retractor 700 is similar to the tissue retractor 100 shown in FIG. 1, therefore components having like reference numerals are not further elaborated.

The tissue retractor 700 differs from the tissue retractor 100 of FIG. 1 in that a different tissue hook 706 is used.

The tissue hook 706 has a tissue engagement portion 706t, which is an adhesive tissue retractor pad, capable of engaging at least a portion of the periphery of tissue (not shown). The tissue hook 706 has a mounting portion 706m. The second end 104s of the retractable member 104 threads through an aperture 706a on the mounting portion 706, causing the second end 104s to loop around the mounting portion 706 to engage the first end 104f and/or the base support unit 102.

It will be appreciated that any suitable tissue hook may be used in conjunction with any of the various exemplary embodiments of the tissue retractor of the present invention. In this regard, the tissue hooks 106, 406, 506 and 706 may include at least one engagement portion with one or more claws [for example, a one to four claw(s)/finger(s) arrangement], where the tissue hook 106, 406, 506 and 706 have a three claw arrangement. Other tissue hooks include a Tyrell delicate prong hook, a Gillies skin hook, a Kilner hook, two-pronged Joseph hooks having prongs that vary between about 2 mm-10 mm in length, Fomon retractors, Rake retractors, Desmarres retractors, or an adhesive tissue retractor pad as shown in the tissue retractor 700 of FIG. 7.

Similarly, the mounting portions 106m, 406m, 506m and 706m of the tissue hooks 106, 406, 506 and 706 that are connected, coupled to or received by their respective retractable members may also take on many forms and is typically dependent upon the type of retractable member used.

Also disclosed is a method of retracting tissue with a tissue retractor as described herein.

With reference to the tissue retractor 100 of FIG. 1, the method includes: attaching the base support unit 102 on a mounting surface (not shown); connecting the retractable member 104 to the mounting portion 106m of the at least one tissue hook 106; engaging the tissue hook 106 with the tissue to be retracted (not shown); retracting the retractable member 104 so that the tissue engagement portion 106t of the tissue hook 106 retracts the tissue to be retracted (not shown) to a predetermined distance.

The method may further include, for example, securing the retracted retractable member 104 to a drape 224 (FIG. 2) via a securing mechanism 220 (FIG. 2). The mounting surface (not shown) may, for example, be a surface proximate to the tissue to be retracted (not shown).

While embodiments of the invention have been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A tissue retraction assembly, comprising:
a hook member formed with a distal tissue engagement feature configured to engage a periphery of an opening in a patient's body such that when the hook member is pulled away from the opening, the distal engagement feature remains in contact with the periphery of the opening to pull the periphery outward, the hook member also being formed with a proximal aperture;
a flexible strap extending through the proximal aperture of the hook member to form a loop, the strap defining first and second end segments; and
a flexible base defining a bottom surface for conforming to a portion of the patient without surrounding the opening in the patient's body, the bottom surface having an adhesive thereon for sticking to a surface, the first end segment of the strap being formed integrally with the base, the second end segment of the strap being removably engageable by hand with a top surface of the base such that the second end segment can be detached from the base by hand, pulled to cinch the loop formed by the strap and thereby pull the hook member to retract tissue away from the opening in the patient's body, and reattached to the top surface of the base by simply pressing the second end segment onto the top surface of the base by hand to thereby hold the loop cinched.

2. The assembly of claim 1, wherein the distal tissue engagement feature includes three curved fingers.

3. A tissue retraction assembly, comprising:
a hook member formed with a distal tissue engagement feature configured to engage a periphery of an opening in a patient's body such that when the hook member is pulled away from the opening, the distal engagement feature remains in contact with the periphery of the opening to pull the periphery outward, the hook member also being formed with a proximal aperture;
a flexible strap extending through the proximal aperture of the hook member to form a loop, the strap defining a first end and a remainder segment extending from the first end to a second end of the strap; and
a flexible base defining a bottom surface for conforming to a portion of the patient without surrounding the opening in the patient's body, the base being wider than the strap, the first end of the strap being made unitarily with the base, the remainder segment of the strap being removably engageable by hand with a top surface of the base such that the remainder segment can be detached from the base by hand, pulled to cinch the loop formed by the strap and thereby pull the hook member to retract tissue away from the opening in the patient's body, and reattached to the top surface of the base by simply pressing the remainder segment onto the top surface of the base by hand to thereby hold the loop cinched.

4. The assembly of claim 3, wherein the distal tissue engagement feature includes three curved fingers.

* * * * *